United States Patent
Dezawa et al.

(10) Patent No.: US 10,641,762 B2
(45) Date of Patent: May 5, 2020

(54) MOBILIZATION OF PLURIPOTENT STEM CELLS FOR ISCHEMIC CEREBRAL INFARCTION

(71) Applicants: UNIVERSITY OF TOYAMA, Toyama (JP); Mari Dezawa, Miyagi (JP); LIFE SCIENCE INSTITUTE, INC., Tokyo (JP)

(72) Inventors: Mari Dezawa, Miyagi (JP); Satoshi Kuroda, Toyama (JP)

(73) Assignees: UNIVERSITY OF TOYAMA, Toyama (JP); Mari Dezawa, Miyagi (JP); LIFE SCIENCE INSTITUTE, INC., Tokyo (JP)

( * ) Notice: Subject to any disclaimer, the term of this patent is extended or adjusted under 35 U.S.C. 154(b) by 0 days.

(21) Appl. No.: 16/070,024

(22) PCT Filed: Jan. 16, 2017

(86) PCT No.: PCT/JP2017/001283
§ 371 (c)(1),
(2) Date: Jul. 13, 2018

(87) PCT Pub. No.: WO2017/122829
PCT Pub. Date: Jul. 20, 2017

(65) Prior Publication Data
US 2019/0025290 A1   Jan. 24, 2019

Related U.S. Application Data

(60) Provisional application No. 62/279,129, filed on Jan. 15, 2016.

(51) Int. Cl.
*G01N 33/50* (2006.01)
*G01N 33/68* (2006.01)

(52) U.S. Cl.
CPC ......... *G01N 33/5073* (2013.01); *G01N 33/68* (2013.01); *G01N 2500/00* (2013.01); *G01N 2800/2871* (2013.01); *G01N 2800/52* (2013.01); *G01N 2800/60* (2013.01)

(58) Field of Classification Search
None
See application file for complete search history.

(56) References Cited

U.S. PATENT DOCUMENTS

2015/0329827 A1   11/2015   Young et al.
2016/0082048 A1   3/2016   Yoshida et al.

FOREIGN PATENT DOCUMENTS

JP   2015-159895 A   9/2015
WO   2014/100806 A1   6/2014

OTHER PUBLICATIONS

Hong et al., A new role of substance P as an injury-inducible messenger for mobilization of CD29+ stromal-like cells, Apr. 2009, Nature Medicine 15(4):425-435 (Year: 2009).*
Kuroda et al., Unique multipotent cells in adult human mesenchymal cell populations, May 11, 2010, PNAS 107(19):8639-8643 (Year: 2010).*
Robey, P. G., Neuropeptide beckons cells that heal, Apr. 2009, Nature Medicine 15(4):1-4 (Year: 2009).*
Yamauchi et al., Therapeutic Effects of Human MultilineageDifferentiating Stress Enduring (MUSE) Cell Transplantation into Infarct Brain of Mice, Mar. 6, 2015, Plos One | DOI:10.1371/journal.pone.0116009, 12 pages (Year: 2016).*
Extended European Search Report dated May 21, 2019 corresponding to EP 17738581.2 filed Jan. 16, 2017; 8 pages.
International Search Report dated Mar. 28, 2017 corresponding to PCT/JP2017/001283 filed Jan. 16, 2017; 2 pages. English translation.
Adams, Volker et al., "Increase of Circulating Endothelial Progenitor Cells in Patients with Coronary Artery Disease After Exercise-Induced Ischemia," *Arterioscler Thromb Vas Biol.* (2004; revision accepted Jan. 24, 2004) 24:684-690.
Aicher, Alexandra et al., "Essential role of endothelial nitric oxide synthase for mobilization of stem and progenitor cells," *Nature Medicine* (Nov. 2003; published online Oct. 12, 2003) 9(11):1370-1376 and Erratum.
Borlongan, Cesar V. et al., "The great migration of bone marrow-derived stem cells toward the ischemic brain: Therapeutic implications for stroke and other neurological disorders," *Progress in Neurobiology* (2011; available online Aug. 30, 2011) 95:213-228.
Chiva-Blanch, Gemma et al., "The non-alcoholic fraction of beer increases stromal cell derived factor 1 and the number of circulating endothelial progenitor cells in high cardiovascular risk subjects: A randomized clinical trial," *Atherosclerosis* (2014; available online Jan. 21, 2014) 233:518-524.
Dunac, Antoine et al., "Neurological and functional recovery in human stroke are associated with peripheral blood CD34+ cell mobilization," *J. Neurol.* (2007; published online Mar. 7, 2007) 254:327-332.
Gojska-Grymajlo, Anna et al., "CD34/CXCR4 stem cell dynamics in acute stroke patients," *Folia Neuropathol* (2012) 50(2):140-146.
Gu, Jain-Wei et al., "Moderate levels of ethanol induce expression of vascular endothelial growth factor and stimulate angiogenesis," *Am J Physiol Regulatory Integrative Comp Physiol* (2001; accepted in final form Apr. 12, 2001) 281:R365-R372.
Hori, Emiko et al., "Mobilization of Pluripotent Multilineage-Differentiating Stress-Enduring Cells in Ischemic Stroke," *Journal of Stroke and Cerebrovascular Diseases*, (Jun. 2016) 25(6):1473-1481.

(Continued)

*Primary Examiner* — John D Ulm
(74) *Attorney, Agent, or Firm* — Mintz Levin Cohn Ferris Glovsky and Popeo PC

(57) ABSTRACT

Provided is a test method comprising a step for measuring the number of SSEA-3-positive pluripotent stem cells present in a blood sample collected from a subject, the test method providing a prognosis for cerebral infarction in the subject, and the diagnosis or prediction of asymptomatic cerebral infarction or the risk of cerebral infarction after a transient ischemic attack in the subject using the number of pluripotent stem cells as an index.

7 Claims, 5 Drawing Sheets

(56) References Cited

OTHER PUBLICATIONS

Huang, Po-Hsun et al., "Moderate intake of red wine improves ischemia-induced neovascularization in diabetic mice—Roles of endothelial progenitor cells and nitric oxide," *Atherosclerosis* (2010; available online Jun. 25, 2010) 212:426-435.

Jedrzejas, Magdalena et al., "Stem cell niches exposed to tobacco smoke," *Przeglad Lekarski* (2012); 69(10):1063-1073.

Jeong, Seon-Yeong et al., "5-Fluorouracil Treatment Leads to Activation of Stem Cell Niche by Reconstructing Mesenchymal Stromal Cells and Exert a Distinct Microenvironmental Impact on Normal and Leukemic Cells," *Blood* (Dec. 3, 2015) 126(3):1197; Abstract only.

Kemp, Kevin et al., "Chemotherapy-induced mesenchymal stem cell damage in patients with hematological malignancy," *Ann Hematol* (2010; published online Jan. 30, 2010) 89:701-713.

Kim, Suk Jae et al., "Circulating Mesenchymal Stem Cells Microparticles in Patients with Cerebrovascular Disease," *Plos ONE* (May 15, 2012) 7(5):e37036; 9 pages.

Kucia, Magda et al., "Cells Expressing Early Cardiac Markers Reside in the Bone Marrow and Are Mobilized Into the Peripheral Blood After Myocardial Infarction," *Circulation Research* (Dec. 2004; accepted Nov. 4, 2004); 10(24):1191-1199.

Kuroda, Satoshi, "Bone marrow stromal cell transplantation for ischemic stroke—its multi-functional feature," *Acta Neurobiol Exp* (2013; accepted Feb. 19, 2013) 73:57-65.

Kuroda, Yasumasa "Mijika na Wadai Sekai no Wadai' (99) Kan'yokei Kansaibo ni Okeru Tayo na Bunka to Soshiki Shufukuno o Ninau MUSE Saibo no Hakken," *Hematology Frontier* (Oct. 30, 2011) 21(11):1664-1669. Concise Statement provided.

Kuroda Yasumasa et al., "Unique multipotent cells in adult human mesenchymal cell populations," *PNAS* (May 11, 2010) 107(19):8639-8643.

Lamirault, Guillaume et al., "Difference in mobilization of progenitor cells after myocardial infarction in smoking versus non-smoking patients: insights from the BONAMI trial," *Stem Cell Research & Therapy* (Dec. 24, 2013) 4:152; 12 pages.

Liu, Zhizhong et al., "Higher numbers of circulating endothelial progenitor cells in stroke patients with intracranial arterial stenosis," *BMC Neurology* (Nov. 5, 2013) 13:161; 7 pages.

Ludwig, Antje et al., "Smoking decreases the level of circulating CD34+ progenitor cells in young healthy women—a pilot study," *BMC Women's Health* (May 30, 2010) 10:20; 8 pages.

Minatoguchi, S. et al., "Abstract: P948 Active cardiac-targeted delivery of sphingosine-1-phosphate attracts Muse cells to the infarcted region and replenishes cardiomyocytes to recover the cardiac function after myocardial infarction," *European Heart Journal* (Aug. 1, 2016) 37 (Abstract Supplement), 180.

Ogura, Fumitaka et al., "Human Adipose Tissue Possesses a Unique Population of Pluripotent Stem Cells with Nontumorigenic and Lw Telomerase Activities: Potential Implications in Regenerative Medicine," *Stem Cells and Development* (2014; prepublished on Liebert Instant Online Nov. 20, 2013) 23(7):717-728.

Paczkowska, Edyta et al., "Clinical Evidence That Very Small Embryonic-Like Stem Cells are Mobilized Into Peripheral Blood in Patients After Stroke," *Stroke* (2009; accepted Sep. 11, 2008) 40:1237-1244.

Strong, Kathleen et al., "Preventing stroke: saving lives around the world," *Lancet Neurol* (Feb. 2007; 6:182-187.

Taguchi, Akihiko et al., "Circulating CD34-Positive Cells Provide an Index of Cerebrovascular Function," *Circulation* (2004; accepted May 11, 2004) 109:2972-2975.

Valenti, Maria Teresa et al., "Mesenchymal stem cells: A new diagnostic tool?" *World J Stem Cells* (Jun. 26, 2015) 7(5):789-792.

Vasa, Mariuca et al., "Number and Migratory Activity of Circulating Endothelial Progenitor Cells Inversely Correlate With Risk Factors for Coronary Artery Disease," *Cir Res.* (2001; accepted Jun. 1, 2001) 89:e1-e7.

Wojakowski, Wojciech et al., "Mobilization of CD34/CXCR4+, CD34/CD117+, c-met+ Stem Cells, and Mononuclear Cells Expressing Early Cardiac, Muscle, and Endothelial Markers Into Peripheral Blood in Patients With Acute Myocardial Infarction," *Circulation* (2004; accepted Sep. 8, 2004) 110:3213-3220.

Wakao, Shohei et al., "Multilineage-differentiating stress-enduring (MUSE) cells are a primary source of induced pluripotent stem cells in human fibroblasts," *PNAS* (Jun. 14, 2011) 108(24):9875-9880.

Yu, Cheol Woong et al., "Cardiovascular event rates in pateints with ST-elevation myocardial infarction were lower with early increases in mobilization of $Oct4^{high}Nanog^{high}$ stem cells into the peripheral circulation during a 4-year follow-up," *International Journal of Cardiology* (2013; available online Apr. 17, 2013) 168:2533-2539.

* cited by examiner

MOBILIZATION OF PLURIPOTENT STEM CELLS FOR ISCHEMIC CEREBRAL INFARCTION

FIELD

The present invention relates to a test method for predicting or diagnosing the prognosis for cerebral infarction in a subject, the risk of cerebral infarction following a transient ischemic attack, or asymptomatic cerebral infarction, and a kit for using the aforementioned test method.

BACKGROUND

Stroke is one of the leading causes of death in humans. 80% or more of all stroke patients suffer ischemic cerebral infarction[1]. Despite the considerable amount of research conducted on the subject, treatment of stroke continues to be limited to thrombolytic therapy performed within 4.5 hours after onset using tissue plasminogen activator (tPA). Supportive care and rehabilitation have only been established for patients in the chronic stage of ischemic cerebral infarction. Thus, an approach involving alternative treatment is required in order to improve the functional outcome of patients.

According to recent research, various stem cells and progenitor cells have been demonstrated to be mobilized from the bone marrow to the peripheral blood in various disorders including ischemic cerebral infarction. These stem cells include endothelial progenitor cells (EPC), hematopoietic stem cells and CD31-positive cells (vascular progenitor cells), and contribute to vascularization in the brain. In addition to these cell types, mesenchymal stem cells (MSC) release neurotrophic factors and enhance functional recovery following ischemic cerebral infarction [2]. More importantly, these MSCs include small numbers of pluripotent cells capable of differentiating into neuronal cells [3]. Recently, Dezawa, et al. discovered a unique type of stem cell in dermal fibroblasts and adult human mesenchymal stem cells such as MSC. These cells account for several percent of all MSC, and since they are resistant to stress, have been named multilineage-differentiating stress enduring (MUSE) cells [4]. These cells can be efficiently isolated as cells positive for stage specific embryonic antigen (SSEA)-3, commonly known cell surface marker for pluripotent stem cells such as human embryonic stem (ES) cells. Muse cells can be efficiently separated from the human bone marrow and dermal fibroblasts by using SSEA-3 antibody in FACS [4]. Muse cells are self-renewable, express genes associated with pluripotency such as Nanog, Oct3/4 or Sox2, and are able to differentiate into endodermal, exodermal and mesodermal cells from a single cell. When induced by cytokines, Muse cells differentiate into neuron marker-positive cells at the extremely high rate of about 90% [5]. According to the results of animal experiments, Muse cells act as tissue repair cells when administrated in vivo. Animal models showed that Muse cells migrate towards damaged tissue, and in several animal disease models, spontaneously differentiate into cells compatible to the tissue they homed after integration into the damaged tissue [4]. In actuality, when injected into the infarcted brains of mice, Muse cells were incorporated in tissue after having settled in the brain of the host, expressed neuron markers, and remarkably enhanced functional recovery [6]. Differing from well known pluripotent stem cells, namely ES cells and induced pluripotent stem (iPS) cells, Muse cells have low telomerase activity and do not form tumors when transplanted into immunodeficient mouse testes [5,7].

SUMMARY

Technical Problem

The inventors of the present invention found that, in ischemic cerebral infarction patients, SSEA-3-positive pluripotent stem cells (Muse cells) are mobilized from the bone marrow to the peripheral blood during the acute stage thereof, thereby leading to completion of the present invention.

Namely, the present invention is as indicated below.

[1] A test method for predicting or diagnosing a prognosis for cerebral infarction in a subject, the risk of cerebral infarction following a transient ischemic attack, or asymptomatic cerebral infarction by using the number of SSEA-3-positive pluripotent stem cells as an indicator, including a step for measuring the number of SSEA-3-positive pluripotent stem cells present in a blood sample collected from the subject.

[2] The test method described in [1] above, wherein the blood sample collected from the subject is collected during the period from immediately to 60 days after the onset of cerebral infarction-like symptoms.

[3] The test method described in [1] or [2] above, wherein the SSEA-3-positive pluripotent stem cells are mobilized from the bone marrow to the peripheral blood during the acute stage of ischemic cerebral infarction.

[4] The test method described in any of [1] to [3] above, wherein prognosis for cerebral infarction is associated with smoking and/or alcohol consumption by the subject.

[5] The test method described in any of [1] to [4] above, further including a step for comparing with a cutoff value.

[6] A kit for use in the test method described in any of [1] to [5] above, containing a reagent enabling measurement of the number of SSEA-3-positive pluripotent stem cells present in a blood sample collected from a subject.

[7] A method for screening for therapeutic drugs for cerebral infarction, including a step for measuring the number of SSEA-3-positive pluripotent stem cells present in a blood sample obtained from a subject after having contacted the subject with a candidate compound of a therapeutic drug for cerebral infarction.

[8] The screening method described in [7] above, further including a step for comparing with a cutoff value.

Advantageous Effects of Invention

The present invention can be used to predict a prognosis for cerebral infarction and diagnose the risk of cerebral infarction caused by a transient ischemic attack, and is also useful for diagnosing asymptomatic cerebral infarction.

DESCRIPTION OF EMBODIMENTS

Figure 1:
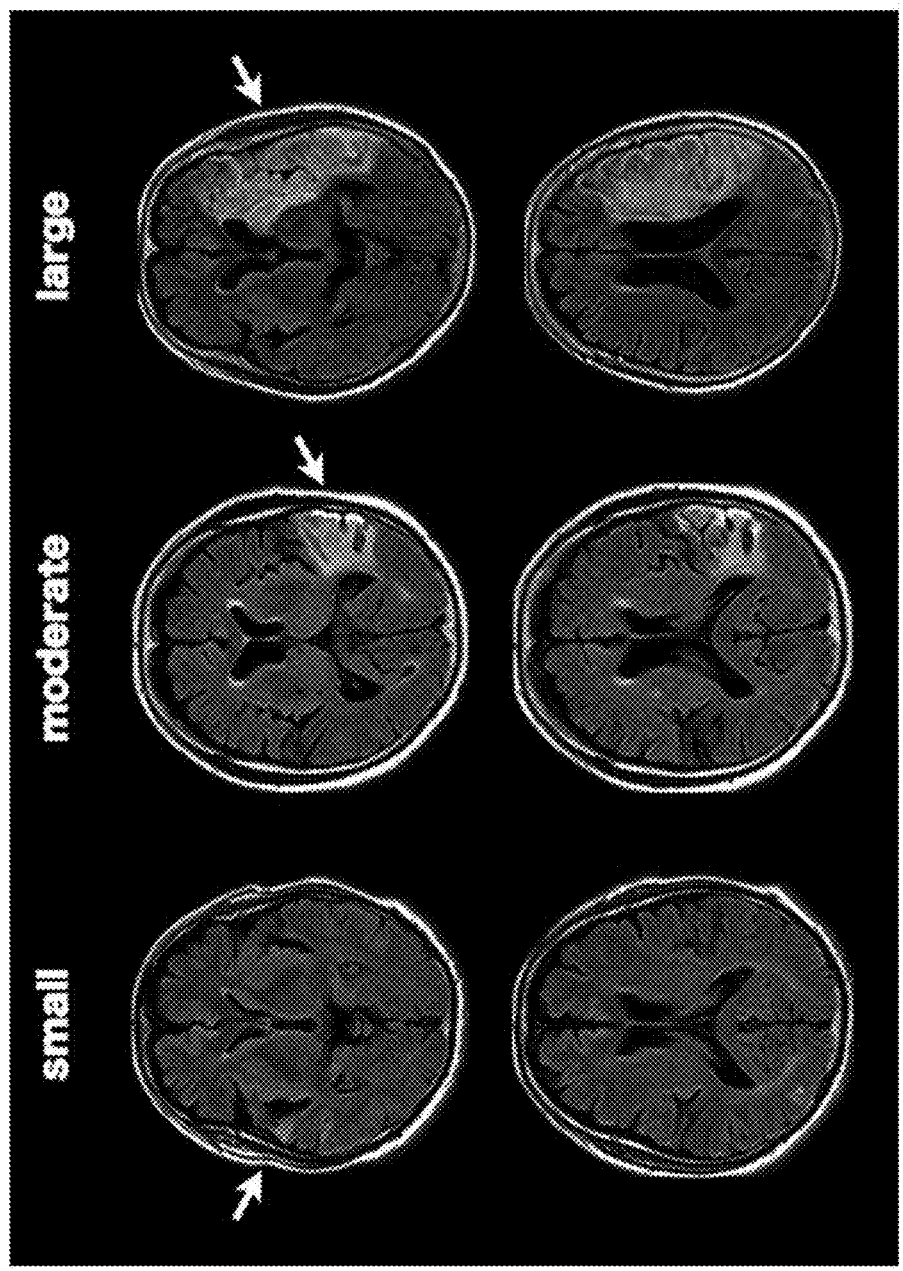
FIG. 1 depicts typical FLAIR images of small-, moderate- and large-sized cerebral infarctions.

The following provides a detailed description of preferred embodiments in order to explain the present invention. Furthermore, the present invention is not limited to the following preferred embodiments, but rather should be understood by a person with ordinary skill in the art to be able to be modified in various ways within the scope of the gist thereof.

The present invention provides a test method for predicting a prognosis for cerebral infarction in a subject based on measuring the number of pluripotent stem cells (Muse cells) mobilized from the bone marrow to the peripheral blood in the subject, and a kit and the like for using the test method.

1. Target Patients

An object of the present invention is to diagnose a prognosis for cerebral infarction, the risk of cerebral infarction based on transient ischemic attach, and asymptomatic cerebral infarction by measuring the number of SSEA-3-positive pluripotent stem cells (Muse cells) in the blood. Here, "cerebral infarction" refers to a state in which a localized ischemic area has formed in the brain causing the subject to present with irreversible cell death of neuronal cells due to cerebrovascular occlusion and decreased perfusion pressure. More specifically, this includes lacunar infarction, which occurs following occlusion of a small artery in the brain, atherothrombotic cerebral infarction, which occurs when a large artery in the brain becomes occluded with plaque, and cardiogenic brain embolism, which occurs when a clot in the heart forms an embolus causing occlusion of a cerebral artery. In addition, cerebral infarctions include an acute stage, subacute stage and recovery stage (chronic stage). In the present invention, a blood sample of a subject is targeted for measurement from immediately after to 60 days after onset. Here, "onset" refers to the time when a subject was last observed in the normal state or when the subject went to bed following the occurrence of cerebral infarction while the patient was asleep in the absence of witnesses. Cerebral infarction is classified into cerebral thrombosis, attributable to thrombosis, and cerebral embolism, and the present invention is useful for diagnosing both cerebral thrombosis and cerebral embolism as well as diagnosing a prognosis for cerebral infarction. A "transient ischemic attack" refers to a transient acute neurological dysfunction caused by a thromboembolism in the cerebral circulation. According to the present invention, the risk of whether or not cerebral infarction has the potential to occur following the onset of such a transient ischemic attack can be diagnosed. In addition, when used in the present description, "asymptomatic cerebral infarction" refers to an ischemic state of brain tissue in the absence of, for example, symptoms characteristic of acute or overt stroke such as hemiparesis, hypesthesia and/or aphasia.

2. Pluripotent Stem Cells

The pluripotent stem cells used in the test method and so forth of the present invention are cells that were discovered by Dezawa, one of the inventors of the present invention, and named multilineage-differentiating stress enduring (Muse) cells. In general, Muse cells can be acquired from the bone marrow fluid, adipose tissue (Ogura, F., et al., Stem Cells Dev., Nov. 20, 2013 (Epub) (published on Jan. 17, 2014)) and the skin including the dermal connective tissue, and are also present in the connective tissue of various organs. In addition, these cells have both the properties of pluripotent stem cells and mesenchymal stem cells, and are identified, for example, as being positive for stage-specific embryonic antigen-3 (SSEA-3) or double positive for SSEA-3 and CD105, each of which are cell surface markers for pluripotent stem cells and mesenchymal stem cells, respectively. Thus, Muse cells and cell populations containing Muse cells can be separated from body tissue by using these antigen markers as indicators. Details regarding separation methods, identification methods and characteristics of Muse cells are disclosed in International Publication No. WO 2011/007900. In addition, as was reported by Wakao, et al. (2011, previously described), in the case of culturing mesenchymal cells from the bone marrow or skin and the like and then using these as a parent population of Muse cells, all the cells positive for SSEA-3 were determined to be positive for CD105. Thus, in the case of separating Muse cells from mesenchymal tissue of the body or cultured mesenchymal stem cells, Muse cells can be purified and used simply by using SSEA-3 as an antigen marker. Furthermore, in the present description, pluripotent stem cells (Muse cells) or a cell population containing Muse cells, which are able to be used in a method for diagnosing cerebral infarction (including sequelae) by using SSEA-3 as an antigen marker and have been separated from body mesenchymal tissue or cultured mesenchymal stem cells, may be described as "SSEA-3-positive cells".

Simply said, Muse cells or cell populations containing Muse cells can be separated from body tissue (such as mesenchymal tissue) either using antibody to the cell surface marker, SSEA-3, alone or using both antibodies to SSEA-3 and CD105, respectively. Here, the "body" refers to a mammalian body. In the present invention, although an embryo in a stage of development prior to a fertilized egg or the blastocyst stage is not included in the term "body", an embryo in a stage of development subsequent to the blastocyst stage, including the fetus and blastula, are included. Examples of mammals include, but are not limited to, humans, monkeys and other primates, mice, rats, rabbits, guinea pigs and other rodents, cats, dogs, sheep, pigs, cows, horses, donkeys, goats and ferrets. Muse cells are clearly distinguished from embryonic stem (ES) cells and iPS cells in that they are separated directly from body tissue by means of a marker. In addition, "mesenchymal tissue" refers to tissue present in various tissues and organs such as bone, periosteum, fat, blood, bone marrow, skeletal muscle, dermis, ligament, tendon, dental pulp, umbilical cord or umbilical cord blood. For example, Muse cells can be acquired from the bone marrow, skin and adipose tissue. For example, Muse cells are preferably used after collecting body mesenchymal tissue and separating Muse cells from this tissue. In addition, Muse cells may also be separated from fibroblasts, bone marrow mesenchymal stem cells or other cultured mesenchymal cells using the aforementioned separation means.

As was previously described, although Muse cells or cell populations containing Muse cells can be separated from body tissue by using SSEA-3 positive and SSEA-3 and CD105 double positive as indicators, Human adult skin is known to include various types of stem cells and progenitor cells in human adult skin. However, Muse cells are not the same as these cells. Examples of these stem cells and progenitor cells include skin-derived progenitors (SKP), neural crest stem cells (NCSC), melanoblasts (MB), pericytes (PC), endothelial progenitors (EP) and adipose-derived stem cells (ADSC). These cells can be distinguished from Muse cells by using "non-expression" of markers unique to these cells as an indicator. More specifically, Muse cells can be separated by using as an indicator the non-expression of at least 1, and for example, 2, 3, 4, 5, 6, 7, 8, 9, 10 or 11 markers selected from the group consisting of CD34 (EP and ADSC marker), CD117 (c-kit) (MB marker), CD146 (PC and ADSC marker), CD271 (NGFR) (NCSC marker), NG2 (PC marker), vWF factor (Von Willebrand factor) (EP marker), Sox10 (NCSC marker), Snail (SKP marker), Slug (SKP marker), Tyrp1 (MB marker) and Dct (MB marker). For example, although not limited thereto, Muse cells can be separated by using non-expression of CD117 and CD146 as an indicator, can be separated using non-expression of CD117, CD146, NG2, CD34, vWF and CD271 as indicators, and can be separated by using non-expression of all of the aforementioned 11 markers as indicators.

Moreover, Muse cells having the aforementioned characteristics may also have at least one property selected from the group consisting of:
(i) low level or absence of telomerase activity,
(ii) ability to differentiate into cell of any of the three germ layers,
(iii) absence of neoplastic proliferation, and
(iv) ability to self-renew.

In one aspect of the present invention, Muse cells have all of the aforementioned properties. Here, with respect to (i) above, a "low level or absence of telomerase activity" refers to only detecting a low level or being unable to detect telomerase activity in the case of having attempted to detect telomerase activity using the Trapeze XL Telomerase Detection Kit (Millipore). Low telomerase activity refers to, for example, having telomerase activity roughly equal to that of somatic cells in the form of human fibroblasts or having telomerase activity equal to $\frac{1}{5}$ or less, and preferably $\frac{1}{10}$ or less, that of Hela cells. With respect to (ii) above, Muse cells have the ability to differentiate into the three germ layers (endoderm, mesoderm and ectoderm) both in vitro and in vivo, and are able to differentiate into liver cells, nerve cells, skeletal muscle cells, smooth muscle cells, osteocytes or adipocytes and the like by, for example, being induced to differentiate by culturing in vitro. In addition, Muse cell may also demonstrate the ability to differentiate into the three germ layers in the case of having transplanted to the testes in vivo. Moreover, Muse cells have the ability to differentiate into cells corresponding to the particular tissue by migrating to and being integrated into the damaged organ (such as the heart, skin, spinal cord, liver or muscle) after having been transplanted into the body by intravenous injection. With respect to (iii) above, although Muse cells have the property of growing at a growth rate of about 1.3 days during suspension culturing, and after growing from a single cell during suspension culturing, form embryoid body-like cell masses after which growth stops in about 14 days, when these embryoid body-like cell masses are subjected to adhesive culturing, cell growth resumes and the cells that grow spread out from the cell mass. Moreover, in the case of transplanting to the testes, Muse cells have the property of not undergoing transformation for at least six months. In addition, with respect to (iv) above, Muse cells typically have the ability to self-renew (self-replicate). Here, self-renewal refers to being able to confirm differentiation from cells contained in the embryoid body-like cell mass, obtained by culturing a single Muse cell by suspension culturing, to cells of the three germ layers, while at the same time being able to confirm the formation of the next-generation embryoid body-like cell mass and subsequent differentiation into the three germ layers again by re-subjecting cells of the embryoid body-like cell mass to suspension culturing from a single cell. Self-renewal may be repeated once or for multiple cycles.

3. Test Method

According to the present invention, a test method is provided for predicting a prognosis for cerebral infarction in a subject by using the number of Muse cells as an indicator, and comprises a step for measuring the number of Muse cells present in a blood sample collected from the subject.

In the aforementioned test method, a "subject" may be any subject provided it is an animal for which there is the possibility for the occurrence of cerebral infarction, and specific examples thereof include humans, monkeys and rodents such as rats. Among these, the test method for cerebral infarction of the present invention is more preferably carried out on humans suspected of cerebral infarction or human presenting with sequelae of cerebral infarction.

A "blood sample" collected from the aforementioned subject contains Muse cells that have been mobilized from the bone marrow into the peripheral blood, and although there are no particular limitations thereon provided it allows the number of Muse cells to be measured, specific examples thereof include plasma such as EDTA plasma or citrated plasma, serum and whole blood. Among these, EDTA plasma is used preferably since it can be collected easily, is easily stored, and allows a large amount to be sampled. The time at which blood is sampled in order to collect the blood sample from a subject may be any time provided it coincides with the time of making a diagnosis of cerebral infarction, and for example, is during the period from immediately to 60 days after the onset of cerebral infarction-like symptoms.

Measuring the number of Muse cells contained in a blood sample can be carried out by, for example, measuring Muse cells contained in a solution collected or stored in a tube containing EDTA using fluorescence-activated cell sorting (FACS). Since the aforementioned collected EDTA solution also contains mononuclear cells in addition to Muse cells, the number of Muse cells can be determined by calculating the percentage of SSEA-3-positive cells among the mononuclear cells. Simply said, the number of Muse cells can be determined with an FACS system by allowing primary antibody in the form of anti-SSEA-3 antibody to react with isolated mononuclear cells followed by reacting with fluorescent-labeled secondary antibody.

As was described above, in the test method of the present invention, cerebral infarction or a prognosis thereof can be tested by measuring the content of Muse cells in a blood sample collected from a subject (and this may also be referred to as a "specimen" in the present description) and then using that content of Muse cells as an indicator. In addition, more accurate testing is possible by combining with the content of existing cerebral infarction markers such as CRP or D-dimer present in a specimen or using as a composite indicator in association with observation of clinical symptoms and the results of other tests such as echocardiography, MRI, MRA or vascular echocardiography of the neck.

As is indicated in Example 2 to be subsequently described, changes in the number of Muse cells can be mainly classified into three patterns according to changes in the number of Muse cells in the blood that have been mobilized from the bone marrow within 30 days after the onset of cerebral infarction. More specifically, these consist of (i) a pattern in which the number of cells decreases significantly after onset (FIG. 3A), (ii) a pattern in which there is no remarkable change observed in the number of cells after onset (FIG. 3B), and (iii) a pattern in which the number of cells increases significantly after onset (FIG. 3C). When these patterns are used in combination with the results of multivariate analysis (see Table 1), increases in the number of SSEA-3-positive cells are significantly inhibited among smokers and significantly promoted among consumers of alcohol on day 7 and/or day 30. In this manner, the test method of the present invention makes it possible to correlate prognosis for cerebral infarction with smoking among smokers and/or the presence or absence of alcohol consumption. Here, when used in the present description, "smoking" in a subject refers to cigarette smoking based on smoking daily within three months prior to onset or hospitalization. In addition, "alcohol consumption" refers to alcohol consumption by a subject in an amount of 150 g per week within the past three months.

In this manner, the present invention provides a test method for predicting prognosis for cerebral infarction. Prognosis for cerebral infarction is indicated with the degree of impairment of a subject attributable to cerebral infarction after the onset of cerebral infarction or after a certain period of time. Degree of impairment can be evaluated using known or previously established indicators. Examples of indicators used include assessment criteria of the Japanese version of the modified Rankin Scale (mRS) (Yukito Shinohara, et al., mRS Reliability Study Group, Research on Reliability of the modified Rankin Scale—Introduction to the Japanese Language Version Assessment Criteria and Questionnaire, Stroke, 2007, 29: 6-13). Here, although "after a certain period of time" refers to any time after onset, from the viewpoint of evaluating the status of the subject's rehabilitation, degree of impairment is typically evaluated during the period from three months to one year after onset. In consideration of usefulness of the prediction method when predicting prognosis, a method is preferably employed in which status of the subject three months after onset, for example, is predicted based on the number of Muse cells present in a blood sample collected from the subject from immediately after to 60 days after onset, although not limited thereto.

Furthermore, in the case of carrying out a test such as predicting prognosis for cerebral infarction as previously described by using the number of Muse cells present in a blood sample collected from a subject as an indicator, a method may be employed in which testing is carried out by comparing with the number of Muse cells present in a blood sample of a healthy individual or by specifying a suitable cutoff value. The number of Muse cells of a healthy individual can be obtained by collecting blood from a healthy individual clinically confirmed in advance to be absent of cerebral infarction and determining the number of Muse cells thereof by treating and measuring in the same manner as blood collected from a subject. Here, "cutoff value" typically refers to a predetermined value used in the case of assessing a target disease group and non-disease group by focusing on a certain substance. In the case of assessing a target disease or the absence thereof, assessment can be made by defining a value equal to or lower than the cutoff value as negative and defining a value equal to or higher than the cutoff value as positive, or conversely, defining a value equal to or lower than the cutoff value as positive and defining a value equal to or higher than the cutoff value as negative.

Figure 3:
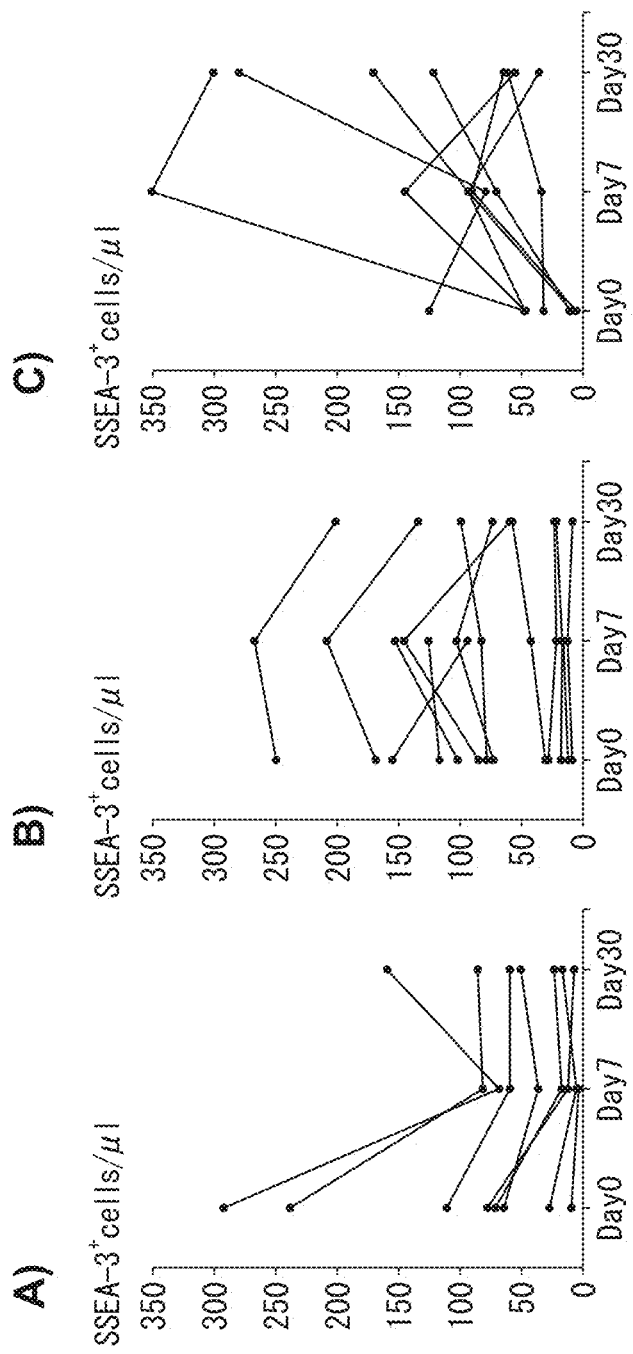
FIG. 3 indicates time-based profiles of SSEA-3-positive cells 30 days after onset of ischemic cerebral infarction. A) represents a group in which SSEA-3 positive cells decreased, B) a group in which they were unchanged, and C) a group in which they increased.

As indicated in Example 2 to be subsequently described, since the number of Muse cells present in the blood of healthy individuals has been determined by measurement to be an average of 3.5±4.3/µl, this value can be used as a cutoff value. FIG. 3 indicates that values higher than the aforementioned value are demonstrated by all cerebral infarction patients and that Muse cells are present in the blood of these patients. Thus, the use of such a cutoff value can be applied to, for example, a diagnosis that a patient is presenting with asymptomatic cerebral infarction and can also be used to evaluate the effect of a cerebral infarction therapeutic drug.

A subject diagnosed with cerebral infarction according to the test method of the present invention can be said to exhibit an extremely favorable prognosis and therapeutic efficacy by undergoing a treatment method suitable for each disease.

4. Cerebral Infarction Assay Kit

The present invention further provides a kit used with the aforementioned test method, containing reagents enabling measurement of Muse cells present in a blood sample collected from a subject, for evaluating the effect of preventing or treating cerebral infarction or a screening method for a preventive or therapeutic drug for cerebral infarction. Although the contents of the kit are composed according to the combination of reagents or measuring instruments, a kit containing substances that are essentially the same as each of the constituents to be subsequently described, or essentially the same as a portion thereof, is also included in the kit of the present invention even if the composition and form may differ. The reagents include anti-SSEA-3 antibody in the case of measuring the number of Muse cells by immunoassay, for example. In addition, the reagents also include a biological sample diluent, antibody-immobilized phase, reaction buffer, washing solution, labeled secondary antibody, label detection reagent or standard substance and the like as necessary. Examples of biological sample diluents include EDTA solution, surfactant or an aqueous solution containing BSA or protein such as casein in a buffer.

The reaction buffer may be any reaction buffer provided it provides a solvent environment during the binding reaction between surface antigen of the Muse cells and the primary antibody, for example. The labeled secondary antibody is an antibody to the aforementioned primary antibody, and antibody labeled with FITC, horseradish peroxidase (HRP), bovine small intestine alkaline phosphatase or β-galactosidase and the like is used.

5. Method for Confirming Therapeutic Efficacy for Cerebral Infarction

Another aspect of the present invention is a method for confirming therapeutic efficacy for cerebral infarction in a subject that comprises a step for measuring the number of Muse cells in a blood sample collected from the subject administered a therapeutic drug for cerebral infarction. The therapeutic drug may be any therapeutic drug provided it is used as a drug capable of treating cerebral infarction, and examples thereof include thrombolytic agents such as urokinase or tissue plasminogen activator, anticoagulants such as heparin, cyclooxygenase inhibitors, phosphorodiesterase inhibitors, anti-platelet agents such as thromboxane A2 (TAX2) and neuroprotective drugs.

A therapeutic drug is judged to demonstrate therapeutic efficacy in the case the number of Muse cells in a blood sample collected from a subject administered a therapeutic drug for cerebral infarction either increases or decreases in comparison with the level prior to administration, or approaches the number of Muse cells in a control subject not presenting with cerebral infarction (such as a healthy individual).

6. Screening of Preventive or Therapeutic Drugs for Cerebral Infarction

Still another aspect of the present invention is a method for screening therapeutic drugs for cerebral infarction that comprises a step for measuring the number of Muse cells in a blood sample of a subject after having contacted the subject with a candidate compound of a therapeutic drug for cerebral infarction. A subject in this screening method can be a non-human animal individual in which the number of Muse cells in a blood sample indicates abnormalities similar to a state of cerebral infarction. Examples of animals having symptoms of cerebral infarction include non-human animal models of cerebral infarction in which a state of cerebral infarction has been formed by a surgical procedure and the like (Yuji Kuge, Kazuo Minematsu, et al., Nylon Monofilament for Intraluminal Middle Cerebral Artery Occlusion in Rats, Stroke, 26, 1655 (1995)). An experiment system for developing a therapeutic drug in a certain type of cerebral infarction patient can be established if it were possible to create a disease state in a non-human animal individual in a state of cerebral infarction (such as a mouse or rat) that mimics a certain disease state in humans. In addition, a therapeutic drug effective for prognosis of cerebral infarction in humans can be developed by determining the prognosis for a non-human animal individual by monitoring the number of Muse cells.

Examples of candidate compounds for use as therapeutic drugs for cerebral infarction that are contacted with these subjects (to also be referred to as "candidate compounds") include peptides, proteins, non-peptide compounds and low molecular weight synthetic compounds, and these compounds may be novel compounds or known compounds. The candidate compound can be judged to have a therapeutic effect against cerebral infarction in the case the number of Muse cells in a subject contacted with the candidate compound increases or decreases in comparison with the level prior to contact or approaches the number of Muse cells in a control subject.

EXAMPLES

Although the following provides a more detailed explanation of the present invention through examples thereof, the present invention is not limited to these examples.

Materials and Methods (1) Subjects

The subjects of this study consisted of 29 adult patients hospitalized for the reason of ischemic cerebral infarction of the supertentorial region within 24 hours after onset. Patients presenting with lacunar infarction were excluded. The subjects consisted of 16 men and 13 women. Their average age was 71.4±13.3 years and their ages ranged from 41 to 93 years old. This study was approved by the ethics committees of the Toyama University Hospital and Saiseikai Toyama Hospital, and informed consent was obtained from each participant.

The inventors of the present invention gathered clinical data for each patient that included age, gender, NIHSS at admission, previous medical history, smoking, alcohol consumption, ischemic cerebral infarction subtype, location and size of cerebral infarction and modified Rankin Score one month after onset. Previous medical history included ischemic and hemorrhagic stroke, hypertension, diabetes mellitus and hyperlipidemia. Hypertension was defined as blood pressure higher than 140/90 mmHg or the current use of an antihypertensive. Diabetes mellitus was defined a hemoglobin A1c value higher than 6.5% or the current use of an antidiabetic drug. Patients having a serum low-density lipoprotein (LDL) cholesterol level higher than 140 mg/dl or patients currently using a hypolipidemic drug were considered to have hyperlipidemia. Patients currently smoking were defined as patients smoking an arbitrary tobacco product based on smoking daily within three months prior to hospitalization. Current alcohol consumption was defined as alcohol consumption in excess of 150 g per day within the past three months.

(2) Physiological and Experimental Data

Blood pressure, ECG and experimental data were recorded for all patients at the time of admission. These tests were repeated 7 days and 30 days after onset.

(3) Radiographic Testing

Diffusion-weighted images, T2-weighted images, fluid-attenuated inversion recovery (FLAIR) images and MR angiographs were obtained for all patients using a 1.5 tesla MR system. The size of the cerebral infarction was divided into three groups consisting of small, moderate and large. The size of the cerebral infarction was graded as large in the case a lesion was located in a region having more than two cortical branches, as moderate in the case a lesion was located in a region having a single cortical branch, and as small in the case of smaller lesions (FIG. 1).

(4) Quantitative Determination of Circulating SSEA-3-Positive Cells 3 ml of peripheral blood were obtained from all patients at the time of admission and on days 7 and 30 in order quantitatively determine the number of circulating SSEA-3-positive cells. The blood was stored in tubes containing ethylenediaminetetraacetic acid (EDTA). In order to isolate mononuclear cells, the blood was diluted with an equal volume of physiological saline followed by layering on 2 ml of Lymphoprep (Axis-Shield Diagnostics Ltd., Scotland) and centrifuging at 800×g for 15 minutes at room temperature. Next, the percentage of SSEA-3-positive cells in the mononuclear cells was determined using fluorescence-activated cell sorting (FACS). Briefly speaking, the isolated mononuclear cells (approx. $1 \times 10^6$) were re-suspended in 100 μl of chilled phosphate-buffered saline (PBS) containing 0.5% bovine serum albumin and 2 mm EDTA (FACS buffer). Primary antibody to SSEA-3 (1:50 dilution, Millipore, MAB4303) was added followed by incubating for 60 minutes at 4° C. while rocking gently. Following binding of primary antibody, the cells were washed twice with FACS buffer, re-suspended in 100 μl of FACS buffer containing 1:100 FITC-bound goat anti-rat IgM (Jackson ImmunoResearch Laboratories, Inc., Baltimore, Pa.), and incubated in a dark location for 60 minutes at 4° C. while rocking gently. Following binding of secondary antibody, the cells were washed three times with chilled FACS buffer followed by re-suspending in 1 ml of chilled FACS buffer, passing through a cell strainer tube (No. 352235, BD Falcon) and immediately analyzing with the FACSCanto™ II (BD Biosciences). A cell control reagent (exposed to secondary antibody only) was used in all FACS analyses to eliminate the possibility of non-specific binding and/or autofluorescence. The number of FITC-positive cells was counted using BD FACSDiva software (BD Biosciences). The absolute number of SSEA-3-positive cells was calculated according to the formula indicated below.

Number of SSEA-3-positive cells on FACS (/μl)=
(Total number of WBC−number of PMN) (/μl)×
SSEA-3-positive cells (%) (in the formula,
PMN represents polymorphonuclear cells).

In this study, peripheral blood was obtained in order to determine the relative value of SSEA-3-positive cells in 5 healthy individuals not having a history of cardiovascular disorders. This blood was collected from 2 men and 3 women and their average age was 56.2±4.2 years. In this study, the absolute number of SSEA-3-positive cells was judged to have increased when that number increased to two or more times the number of cells of the control at the time of admission on day 7 or day 30, and was judged to have decreased when that number was less than half the control at the time of admission on day 7 or day 30.

(5) Histological Analysis

In order to determine the percentage and distribution of SSEA-3-positive cells in the human bone marrow, specimens were obtained from 8 autopsied patients not having a history of cerebrovascular disease. These patients consisted of 5 men and 3 women. Their average age was 63.9±9.0 years and their ages ranged from 57 to 73 years old. These patients died due to various diseases such as myocardial infarction, malignant tumor or heart failure. The specimens were fixed with buffered formalin (4%) and embedded in paraffin. Subsequently, sections having a thickness of 4 μm were prepared for subsequent staining. The de-paraffinized sections were treated by recovering antigen for 2 minutes with a pressure pot. SSEA-3-positive cells in the human bone marrow were identified using immunohistochemical staining. Briefly speaking, after treating each section with primary antibody to SSEA-3 (rat monoclonal antibody, 1:100 dilution, Millipore, MAB4303) overnight at 4° C., the sections were incubated with fluorescein (FITC) AffiniPure (goat anti-rabbit IgM, 1:50 dilution, Jackson Immunoresearch) for 1 hour at room temperature. Finally, the sections were stained for 24 hours at room temperature using Pro-Long Gold Antifade reagent containing DAPI. The percentage of SSEA-3-positive cells among all the bone marrow cells was calculated in five randomly selected fields using a microscope (BZ9000, Keyence Co., Osaka, Japan) at a magnification factor of 20×.

(6) Statistical Analysis

Data was expressed as the mean±SD. Categorical variables were compared using the $\chi^2$ test. Continuous variables were compared using the two-sided unpaired t-test between two groups and single factor ANOVA among three groups. A P value of less than 0.05 was considered to constitute a statistically significant difference.

Important factors for predicting the number of circulating SSEA-3-positive cells at the time of admission were identified by carrying out multiple linear regression analyses. Moreover, independent factors for determining increases in circulating SSEA-3-positive cells on day 7 or day 30 following the onset of ischemic cerebral infarction were identified by carrying out multivariate logistic regression analyses. The method used to create a forward step-by-step model was carried out for each parameter using a value of P<0.40 obtained by multivariate analysis. During the final multivariate analysis, a value of P<0.05 was set for the level of statistical significance. Results were expressed in the form of the adjusted odds ratio (OR) and corresponding 95% confidence interval (CI).

Example 1: Clinical Characteristics

The average NIHSS at admission was 8.6±7.4 and NIHSS ranged from 0 to 24. Clinical diagnoses included coronary embolism in 17 patients, atherothrombotic stroke in 7 patients, aortic embolism in 3 patients and other diseases in 2 patients. Previous medical history consisted of hypertension in 16 patients, diabetes in 3 patients, hyperlipidemia in 4 patients, smoking in 7 patients and alcohol consumption in 10 patients.

Average mRS on day 30 was 2.3±2.2 and scores ranged from 0 to 6. Two patients (6.9%) died on day 8 to 30 following onset and their data was analyzed in this study only for time of admission and day 7. Size of cerebral infarction was small in 13 patients, moderate in 10 patients and large in 6 patients.

Example 2: Circulating SSEA-3-Positive Cells

Figure 2:
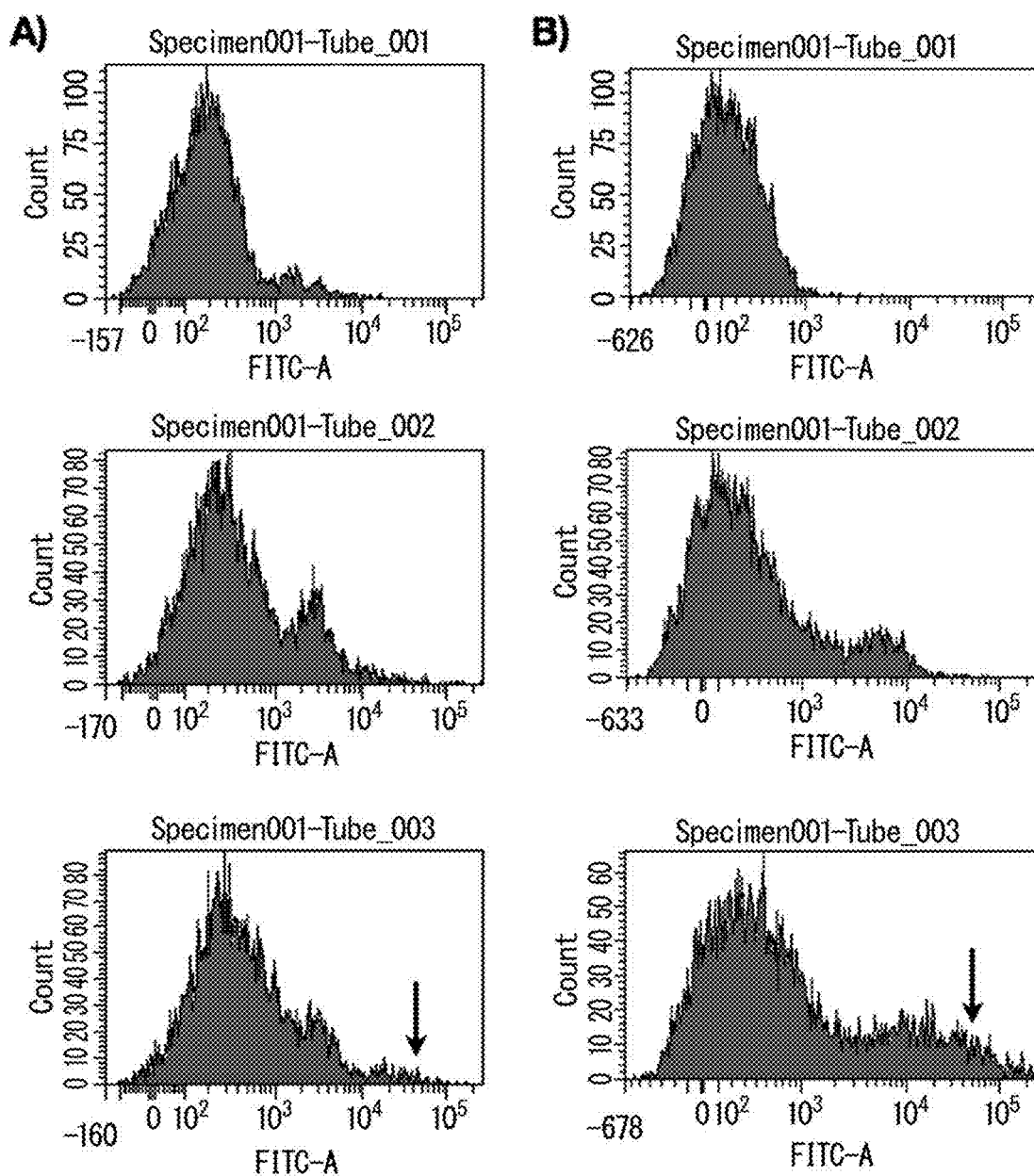
FIG. 2 indicates typical FACS data in healthy individuals (A) and patients with ischemic cerebral infarction (B). The upper graphs represent cell count data of a control, the middle graphs represent cell count data having only secondary antibody, and the lower graphs represent cell count data having primary and secondary antibodies. SSEA-3-positive cells are identified in the lower graphs (arrows).

FIG. 2 indicates typical FACS analysis results in control patients and patients with ischemic cerebral infarction. In the healthy individual controls, the number of SSEA-3-positive cells was extremely low, ranging from 0/μl to 10/μl. The average value was 3.5±4.3/μl. On the other hand, the baseline number of SSEA-3-positive cells at admission differed considerably between patients. The average value of SSEA-3-positive cells at admission was 81.9±78.0/μl and ranged from 4.7/μl to 249.1/μl. Thus, in 22 of the 29 subjects (75.9%), the number of SSEA-3-positive cells increased remarkably within 24 hours after onset of ischemic cerebral infarction. According to the results of multivariate analyses, there were no significant correlations detected between the number of SSEA-3-positive cells at admission and age, gender, NIHSS at admission, past medical history, ischemic cerebral infarction subtype, size of cerebral infarction or mRS on day 30. Multiple linear regression analyses did not identify important factors for predicting the absolute number of circulating SSEA-3-positive cells at admission.

The number of circulating SSEA-3-positive cells was evaluated continuously for up to 30 days after onset. These values changed from 81.9±78.0/μl to 86.9±80.8/μl and 68.7±64.9/μl on days 7 and 30, respectively. There were no significant differences among measurement times. FIG. 3 indicates time-based profiles of circulating SSEA-3-positive cells. Kinetics was able to be divided into three patterns. The number of circulating SSEA-3-positive cells in 8 of the 29 patients (27.6%) decreased significantly on day 7. This number did not recover on day 30 in 7 of these 8 patients. In 13 of the 29 patients (44.8%), there were no changes in the number of SSEA-3-positive cells within 30 days after onset and levels remained higher than the control. However, in 8 of the 29 patients (27.6%), the number of circulating SSEA-3-positive cells continued to increase significantly on day 7 and/or day 30. As shown in Table 1, according to the results of univariate analyses, important factors for predicting a continuous increase in circulating SSEA-3-positive cells for 30 days after the onset of ischemic cerebral infarction were not identified. However, multivariate logistic regression analyses indicated that current smoking and alcohol consumption have a significant effect on a continuous increase in circulating SSEA-3-positive cells within 30 days after onset. Odds ratios consisted of 0.0027 (P=0.0336, 95%

CI=0-0.633) for current smoking and 1.688 (P=0.220, 95% CI=2.91-978.046) for current alcohol consumption.

tumor. When these three patients are excluded, although not statistically significant, there tended to be a negative corre-

TABLE 1

| | Circulating SSEA-3+ Cells | | | | |
|---|---|---|---|---|---|
| | Increase (n = 8) | No increase (n = 21) | Univariate analysis | Multivariate analysis | OR (95% CI) |
| Age (years) | 69.6 ± 12.6 | 72.1 ± 13.8 | P = 0.657 | | |
| Gender | | | | | |
| Men | 4 | 12 | P = 0.943 | | |
| Women | 4 | 9 | | | |
| Hypertension | | | | | |
| Present | 5 | 11 | P = 0.942 | | |
| Absent | 3 | 19 | | | |
| Diabetes mellitus | | | | | |
| Present | 0 | 3 | P = 0.654 | | |
| Absent | 8 | 18 | | | |
| Hyperlipidemia | | | | | |
| Present | 2 | 2 | P = 0.632 | | |
| Absent | 6 | 19 | | | |
| Smoking | | | | | |
| Yes | 1 | 6 | P = 0.366 | P = 0.0366 | 0.0027 (0-0.633) |
| No | 7 | 15 | | | |
| Alcohol consumption | | | | | |
| Yes | 5 | 5 | P = 0.128 | P = 0.0220 | 1688 (2.91-978.046) |
| No | 3 | 16 | | | |
| Cerebral infarction subtype | | | | | |
| Atherothrombotic | 2 | 5 | P = 0.171 | P = 0.931 | |
| Cardiogenic | 3 | 14 | | | |
| Aortogenic | 2 | 0 | | | |
| Other | 1 | 2 | | | |
| NIHSS score at admission | 6.9 ± 3.0 | 9.2 ± 1.9 | P = 0.518 | | |
| Infarction size | | | | | |
| Small | 4 | 9 | P = 0.809 | | |
| Moderate | 2 | 8 | | | |
| Large | 2 | 4 | | | |
| One-month mRS | | | | | |
| 0 | 5 | 6 | P = 0.297 | P = 0.877 | |
| 1 | 0 | 2 | | | |
| 2 | 1 | 0 | | | |
| 3 | 1 | 4 | | | |
| 4 | 1 | 3 | | | |
| 5 | 0 | 4 | | | |
| 6 | 0 | 2 | | | |

Figure 4:
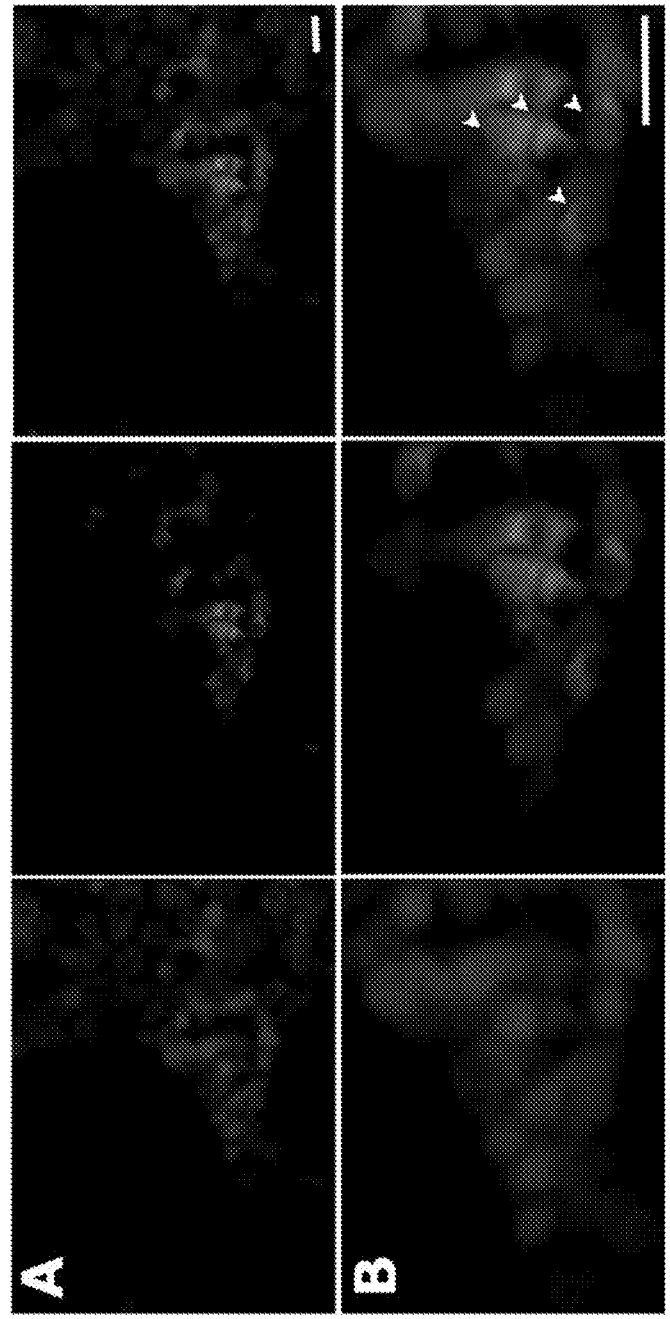
FIG. 4 depicts fluorescent immunohistochemical micrographs of the human bone marrow exhibiting small fragments of SSEA-3-positive cells (green). The scale bar represents a distance of 50 μm.
Figure 5:
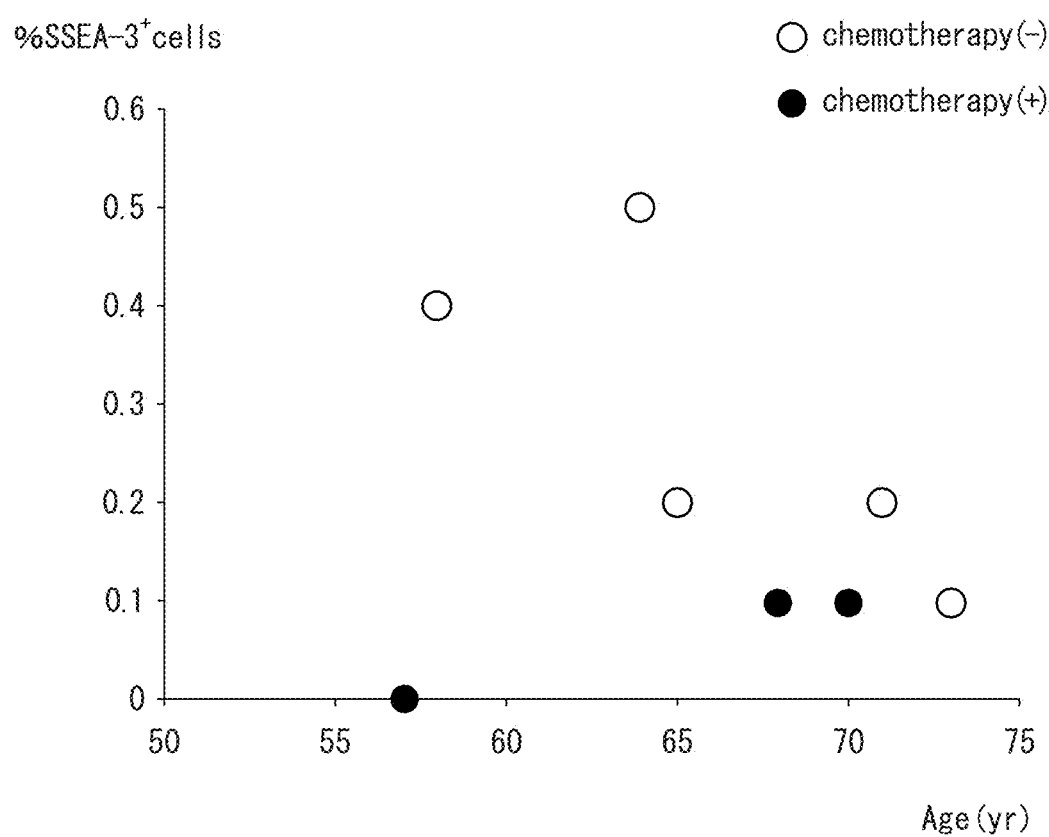
FIG. 5 indicates the relationship between age and percent of SSEA-3-positive cells in the bone marrow. The white circles represent data of patients that did not undergo chemotherapy, while the black circles represent data of patients that underwent chemotherapy.

Independent prediction factors for increases in circulating SSEA-3-positive cells following ischemic cerebral infarction OR: Odds ratio, CI: Confidence interval Example 3: Distribution of SSEA-3-Positive Cells in the Human Bone Marrow A small fraction of bone marrow cells was positive for SSEA-3. As shown in FIG. 4, the distribution of SSEA-3-positive cells was not uniform. These cells were distributed in the manner of clusters. The percentage of SSEA-3-positive cells changed from 0% to 0.5% and the average value thereof was 0.2±0.17%. As shown in FIG. 5, the percentage of SSEA-3-positive cells was less than 0.1% in three patients that underwent chemotherapy for a malignant tumor. When these three patients are excluded, although not statistically significant, there tended to be a negative correlation between patient age and the percentage of SSEA-3-positive cells in bone marrow.

Discussion

In this study, the bone marrow specimens were stained using primary antibody to SSEA-3. This is because a previous study did not indicate localization of Muse cells in the bone marrow. As a result, this research indicated that SSEA-3-positive cells correspond to about 0.2% of all the bone marrow cells. According to a previous study, Muse cells are identified at the rate of 0.03% in the human bone marrow aspirate and are identified at the rate of 5% to 6% among MSC[5]. Although these populations tend to gradually decrease with age, statistical significance was not obtained probably due to the small sample size. It is interesting to note that, since chemotherapy and radiation therapy have the potential to cause long-term damage to the bone marrow cells, including stem cells/progenitor cells and MSC, the size of the Muse cell population in patients undergoing chemotherapy for a malignant tumor was extremely small [8]. Thus, there are cases in which even SSEA-3-positive cells are subject to irreversible and sustained damage following chemotherapy.

At present, stem cells/progenitor cells in the bone marrow are commonly known to be rapidly mobilized into peripheral blood in various diseases including ischemic cerebral infarction[2]. Non-hematopoietic stem cells expressing early progenitor cell markers are mobilized from the bone marrow into the peripheral blood following acute myocardial infarction[9,10] and ischemic cerebral infarction[11]. Recently, Yu, et al. (2013) isolated peripheral blood mononuclear cells from acute myocardial infarction patients on day 0, day 1 and day 7 and measured mRNA expression of embryonic stem cell markers. They reported that mRNA levels of Oct4, Nanog, CD31 and VE-cadherin were significantly higher in peripheral blood on day 0 and day 1[12]. Moreover, a similar phenomenon was also observed in patients with ischemic cerebral infarction [13,14]. Current findings resemble this previous data. Thus, the number of circulating SSEA-3-positive cells was extremely high at the time of admission in comparison with the control in 22 of 29 ischemic cerebral infarction patients.

In this study, baseline levels of the number of SSEA-3-positive cells at admission differed considerably among ischemic cerebral infarction patients. Clinical parameters were unable to predict the baseline level of SSEA-3-positive cells. Kinetics within 30 days after onset also varied considerably depending on the patient. These results demonstrate a favorable correlation with previous studies. Thus, Dunac, et al. (2007) evaluated mobilization of CD34-positive cells in 25 ischemic cerebral infarction patients and found that the number of cells fluctuated considerably each day between each patient and within a single patient [15]. However, this study indicated that in 8 of 29 patients (27.6%), SSEA-3-positive cells were definitively and continuously mobilized in peripheral blood for 30 days following onset of ischemic cerebral infarction (FIG. 2). In contrast, a previous study indicated that mobilization of stem cell/progenitor cells, including endothelial progenitor cells, reached a peak 24 to 48 hours after onset and returned to the control level in patients with acute myocardial infarction [16]. Taguchi, et al. (2004) reported that CD34-positive cells increased continuously for 7 days and subsequently decreased to baseline levels on day 30[13]. Thus, the time-based profile of mobilization of stem cells/progenitor cells is greatly dependent on patient status and the type of mobilized cells.

According to previous studies, mobilization of endothelial progenitor cells was shown to be controlled by various factors including age and diabetes mellitus. Although opposing results have also been reported, all of these factors are thought to inhibit mobilization [17,18]. However, in this study, all of these factors did not correlate with the time-based profile of SSEA-3-positive cells. Instead, this study indicated that smoking and alcohol consumption greatly affect the kinetics of SSEA-3-positive cells following ischemic cerebral infarction. Thus, smoking significantly prevented increases in the number of SSEA-3-positive cells on day 7 and/or day 30 while alcohol consumption significantly promoted these increases. In actuality, numerous previous studies strongly suggest effects on the biological characteristics of stem cells/progenitor cells attributable to smoking and alcohol consumption. Ludwig, et al. (2010) reported that the number of circulating CD34-positive cells is significantly lower in smokers than in non-smokers [19]. Lamirault, et al. (2013) reported a correlation between active smoking and low levels of CD-34-positive cells in the bone marrow and blood [20]. The deleterious effects of smoking on stem cells/progenitor cells include a direct effect on cells and control mechanisms thereof as well as changes in the microenvironment thereof. Exposure of stem cells/progenitor cells to smoke components has the potential to bring about a decrease in the number and quality of these cells in tissue reservoirs [21]. There are several hypotheses for explaining this mechanism of action. Among these, the production of reactive oxygen species (ROS) associated with smoking has the possibility of decreasing the bioavailability of nitrogen oxide (NO) and reducing mobilization from the bone marrow [22]. Alcohol abuse also has a detrimental effect on human health. However, immunological studies have shown that moderate consumption of ethanol lowers the risk of coronary heart disease, sudden cardiac death and ischemic cerebral infarction. In actuality, moderate amounts of ethanol enhance vascularization in cultured cells [23]. Moreover, Chiva-Blanch, et al. (2014) reported that the non-alcohol fraction of beer increases the number of circulating endothelial cells in patients at high cardiovascular risk [24]. Moderate consumption of red wine also improves mobilization of cells in diabetic mice [25]. Thus, several components contained in alcohol are able to contribute to mobilization of stem cells/progenitor cells and ethanol per se.

In this study, continuous increases in the number of Muse cells did not directly correlate with a more favorable functional outcome. However, according to recent observations, the kinetics of stem cells/progenitor cells in the peripheral blood has the possibility of playing an important role in the process by which ischemic cerebral lesions occur [14]. Thus, Dunac, et al. (2007) measured circulating CD34-positive cells and concluded that the degree of the mobilization thereof is directly related to functional recovery following ischemic cerebral infarction [15]. Gojska-Grymajio, et al. (2012) also reported that increased mobilization of CD34-positive and CD34/CXCR4-positive cells is related to a more favorable functional outcome [14]. Thus, although these "highly responsive" patients are characterized by a favorable functional outcome following ischemic cerebral infarction, it is necessary to demonstrate that mobilized cells in these patients migrate towards the infarcted lesion and regenerate damaged brain in humans. A broader study will likely clarify whether or not mobilization of SSEA-3-positive cells is able to contribute to functional recovery following ischemic cerebral infarction.

Conclusion

This study clearly showed that pluripotent Muse cells are mobilized from the bone marrow to the peripheral blood during the acute stage of ischemic cerebral infarction. Smoking and alcohol consumption have a significant effect on the time-based profile of Muse cells. In this study, the baseline number and kinetics of SSEA-3-positive cells probably do not correlate with functional outcome due to the small amount thereof in the peripheral blood. However, therapeutic intervention for increasing endogenous Muse cells or exogenous administration of Muse cells is a novel treatment strategy for improving functional outcome following ischemic cerebral infarction.

Disclosure of all of the previously indicated reference documents and corresponding patent applications are incorporated in the present description in their entirety by reference.

REFERENCES

[1] Strong K, Mathers C, Bonita R. Preventing stroke: saving lives around the world. Lancet Neurol. 2007; 6:182-7.
[2] Borlongan C V, Glover L E, Tajiri N, Kaneko Y, Freeman T B. The great migration of bone marrow-derived stem cells toward the ischemic brain: therapeutic implications for stroke and other neurological disorders. Progress in neurobiology. 2011; 95:213-28.
[3] Kuroda S. Bone marrow stromal cell transplantation for Ischemic Stroke—its multi-functional feature. Acta Neurobiol Exp (Wars). 2013; 73:57-65.
[4] Kuroda Y, Kitada M, Wakao S, Nishikawa K, Tanimura Y, Makinoshima H, et al. Unique multipotent cells in adult human mesenchymal cell populations. Proc Natl Acad Sci USA. 2010; 107:8639-43.
[5] Wakao S, Kitada M, Kuroda Y, Shigemoto T, Matsuse D, Akashi H, et al. Multilineage-differentiating stress-enduring (Muse) cells are a primary source of induced pluripotent stem cells in human fibroblasts. Proc Natl Acad Sci USA. 2011; 108:9875-80.
[6] Yamauchi T, Kuroda Y, Morita T, Shichinohe H, Houkin K, Dezawa M, et al. Therapeutic effects of human multilineage-differentiating stress enduring (MUSE) cell transplantation into infarct brain of mice. PLoS One. in press.
[7] Ogura F, Wakao S, Kuroda Y, Tsuchiyama K, Bagheri M, Heneidi S, et al. Human adipose tissue possesses a unique population of pluripotent stem cells with nontumorigenic and low telomerase activities: potential implications in regenerative medicine. Stem Cells Dev. 2014; 23:717-28.
[8] Kemp K, Morse R, Wexler S, Cox C, Mallam E, Hows J, et al. Chemotherapy-induced mesenchymal stem cell damage in patients with hematological malignancy. Annals of hematology. 2010; 89:701-13.
[9] Kucia M, Dawn B, Hunt G, Guo Y, Wysoczynski M, Majka M, et al. Cells expressing early cardiac markers reside in the bone marrow and are mobilized into the peripheral blood after myocardial infarction. Circ Res. 2004; 95:1191-9.
[10] Wojakowski W, Tendera M, Michalowska A, Majka M, Kucia M, Maslankiewicz K, et al. Mobilization of CD34/CXCR4+, CD34/CD117+, c-met+ stem cells, and mononuclear cells expressing early cardiac, muscle, and endothelial markers into peripheral blood in patients with acute myocardial infarction. Circulation. 2004; 110:3213-20.
[11] Paczkowska E, Kucia M, Koziarska D, Halasa M, Safranow K, Masiuk M, et al. Clinical evidence that very small embryonic-like stem cells are mobilized into peripheral blood in patients after stroke. Stroke. 2009; 40:1237-44.
[12] Yu C W, Choi S C, Hong S J, Choi J H, Park C Y, Kim J H, et al. Cardiovascular event rates in patients with ST-elevation myocardial infarction were lower with early increases in mobilization of Oct4(high)Nanog(high) stem cells into the peripheral circulation during a 4-year follow-up. International journal of cardiology. 2013; 168:2533-9.
[13] Taguchi A, Matsuyama T, Moriwaki H, Hayashi T, Hayashida K, Nagatsuka K, et al. Circulating CD34-positive cells provide an index of cerebrovascular function. Circulation. 2004; 109:2972-5.
[14] Gojska-Grymajlo A, Nyka W M, Zielinski M, Jakubowski Z. CD34/CXCR4 stem cell dynamics in acute stroke patients. Folia neuropathologica/Association of Polish Neuropathologists and Medical Research Centre, Polish Academy of Sciences. 2012; 50:140-6.
[15] Dunac A, Frelin C, Popolo-Blondeau M, Chatel M, Mahagne M H, Philip P J. Neurological and functional recovery in human stroke are associated with peripheral blood CD34+ cell mobilization. Journal of neurology. 2007; 254:327-32.
[16] Adams V, Lenk K, Linke A, Lenz D, Erbs S, Sandri M, et al. Increase of circulating endothelial progenitor cells in patients with coronary artery disease after exercise-induced ischemia. Arteriosclerosis, thrombosis, and vascular biology. 2004; 24:684-90.
[17] Vasa M, Fichtlscherer S, Aicher A, Adler K, Urbich C, Martin H, et al. Number and migratory activity of circulating endothelial progenitor cells inversely correlate with risk factors for coronary artery disease. Circ Res. 2001; 89:E1-7.
[18] Liu Z, Ding X, Fang F, Wang R, Chen Y, Ma Y, et al. Higher numbers of circulating endothelial progenitor cells in stroke patients with intracranial arterial stenosis. BMC neurology. 2013; 13:161.
[19] Ludwig A, Jochmann N, Kertesz A, Kuhn C, Mueller S, Gericke C, et al. Smoking decreases the level of circulating CD34+ progenitor cells in young healthy women—a pilot study. BMC women's health. 2010; 10:20.
[20] Lamirault G, Susen S, Forest V, Hemont C, Parini A, Le Corvoisier P, et al. Difference in mobilization of progenitor cells after myocardial infarction in smoking versus non-smoking patients: insights from the BONAMI trial. Stem cell research & therapy. 2013; 4:152.
[21] Jedrzejas M, Skowron K, Czekaj P. Stem cell niches exposed to tobacco smoke. Przeglad lekarski. 2012; 69:1063-73.
[22] Aicher A, Heeschen C, Mildner-Rihm C, Urbich C, Ihling C, Technau-Ihling K, et al. Essential role of endothelial nitric oxide synthase for mobilization of stem and progenitor cells. Nat Med. 2003; 9:1370-6.
[23] Gu J W, Elam J, Sartin A, Li W, Roach R, Adair T H. Moderate levels of ethanol induce expression of vascular endothelial growth factor and stimulate angiogenesis. American journal of physiology Regulatory, integrative and comparative physiology. 2001; 281:R365-72.
[24] Chiva-Blanch G, Condines X, Magraner E, Roth I, Valderas-Martinez P, Arranz S, et al. The non-alcoholic fraction of beer increases stromal cell derived factor 1 and the number of circulating endothelial progenitor cells in high cardiovascular risk subjects: a randomized clinical trial. Atherosclerosis. 2014; 233:518-24.
[25] Huang P H, Tsai H Y, Wang C H, Chen Y H, Chen J S, Lin F Y, et al. Moderate intake of red wine improves ischemia-induced neovascularization in diabetic mice—roles of endothelial progenitor cells and nitric oxide. Atherosclerosis. 2010; 212:426-35.

The invention claimed is:

1. A test method for predicting or diagnosing a prognosis for cerebral infarction in a subject, the risk of cerebral infarction following a transient ischemic attack, or asymptomatic cerebral infarction, the method comprising the steps:

a) collecting a blood sample from the subject;
b) measuring the number of SSEA-3-positive pluripotent stem cells present in the blood sample collected from the subject; and
c) comparing the number of the measured pluripotent stem cells with a cutoff value: 3.5±4.3/µl and determining that the test is positive if it is higher than the cutoff value, wherein the pluripotent stem cells have all of the following properties:
(i) SSEA-3 positive;
(ii) CD105 positive;
(iii) low or absent telomerase activity;
(iv) ability to differentiate into cells of any of the three germ layers;
(v) absence of demonstration of neoplastic proliferation; and
(vi) presence of self-renewal ability.

2. The test method according to claim 1, wherein the blood sample collected from the subject is collected during the period from immediately to 60 days after the onset of cerebral infarction-like symptoms.

3. The test method according to claim 1 or 2, wherein the SSEA-3-positive pluripotent stem cells are mobilized from the bone marrow to the peripheral blood during the acute stage of ischemic cerebral infarction.

4. The test method according to claim 1, wherein prognosis for cerebral infarction is associated with smoking and/or alcohol consumption by the subject.

5. The test method according to claim 1, further comprising a step for comparing with a cutoff value.

6. A method of treating a cerebral infarction in a subject, the method comprising:

a) collecting a blood sample from the subject;
b) measuring the number of SSEA-3-positive pluripotent stem cells present in the blood sample collected from the subject;
c) comparing the number of the measured pluripotent stem cells with a cutoff value: $3.5\pm4.3/\mu l$ and determining that the test is positive if it is higher than the cutoff value; and
d) if the test is positive, administering a drug capable of treating a cerebral infarction to the subject;
wherein the pluripotent stem cells have all of the following properties:
(i) SSEA-3 positive;
(ii) CD105 positive;
(iii) low or absent telomerase activity;
(iv) ability to differentiate into cells of any of the three germ layers;
(v) absence of demonstration of neoplastic proliferation; and
(vi) presence of self-renewal ability.

7. The method of claim 6, wherein the drug capable of treating a cerebral infarction is selected from the group consisting of thrombolytic agents, anticoagulants, cyclooxygenase inhibitors, phosphorodiesterase inhibitors, anti-platelet agents, and neuroprotective drugs.

* * * * *